United States Patent [19]

Purgold

[11] 4,274,285
[45] Jun. 23, 1981

[54] AUTOMATED SYRINGE SAMPLER

[75] Inventor: Gerald C. Purgold, Newport News, Va.

[73] Assignee: The United States of America as represented by the Administrator of the National Aeronautics and Space Administration, Washington, D.C.

[21] Appl. No.: 111,438

[22] Filed: Jan. 11, 1980

[51] Int. Cl.³ .............................................. G01N 1/14
[52] U.S. Cl. ............................... 73/683.31; 73/684.52
[58] Field of Search ........................ 73/425.6, 425.4 P; 128/762, 764

[56] References Cited

U.S. PATENT DOCUMENTS

| | | | |
|---|---|---|---|
| 3,001,403 | 9/1961 | Edwards | 73/425.6 |
| 3,696,806 | 10/1972 | Sausse | 128/762 |
| 3,765,402 | 10/1973 | Grabhorn | 128/762 |
| 3,884,081 | 5/1975 | Griffith | 73/421.5 R |
| 4,079,729 | 3/1978 | Cornell | 128/764 |

*Primary Examiner*—S. Clement Swisher
*Attorney, Agent, or Firm*—Howard J. Osborn; John R. Manning; Wallace J. Nelson

[57] ABSTRACT

The invention is housed within a housing 11 and positionable within a test fluid medium where pump 23 causes continuous test fluid flow therethrough via inlet filters 29 and conduit 27. A plurality of sampling devices 25 are disposed on rack 16 slidably received in housing 11 and are responsive to a remote signal received through antenna 32 to receiver 60 to activate circuitry elements. When activated the circuitry provides power individually, collectively or selectively to servo mechanisms 56 thereby moving actuator arm 52 and its attached jawed bracket 51 supporting evacuated tube 46 toward stationary needle 39. One open end of needle 39 extends through the sidewall of conduit 27 to the interior thereof and the other open end is maintained within protective sleeve 41 supported by bifurcated bracket 49. Septum 46 is punctured by the open end of needle 39 contained within protective sleeve 41 and a sample of the fluid test medium in conduit 27 flows through needle 39 and is transferred to tube 46. The signal to servo 56 is then reversed and actuator arm 52 moves tube 46 back to its original position permitting septum 45 to expand and seal the hole made by needle 39. Jawed bracket 51 is pivotally attached to actuator arm 52 as shown in FIGS. 3 and 4 to facilitate replacement of tubes 46.

9 Claims, 5 Drawing Figures

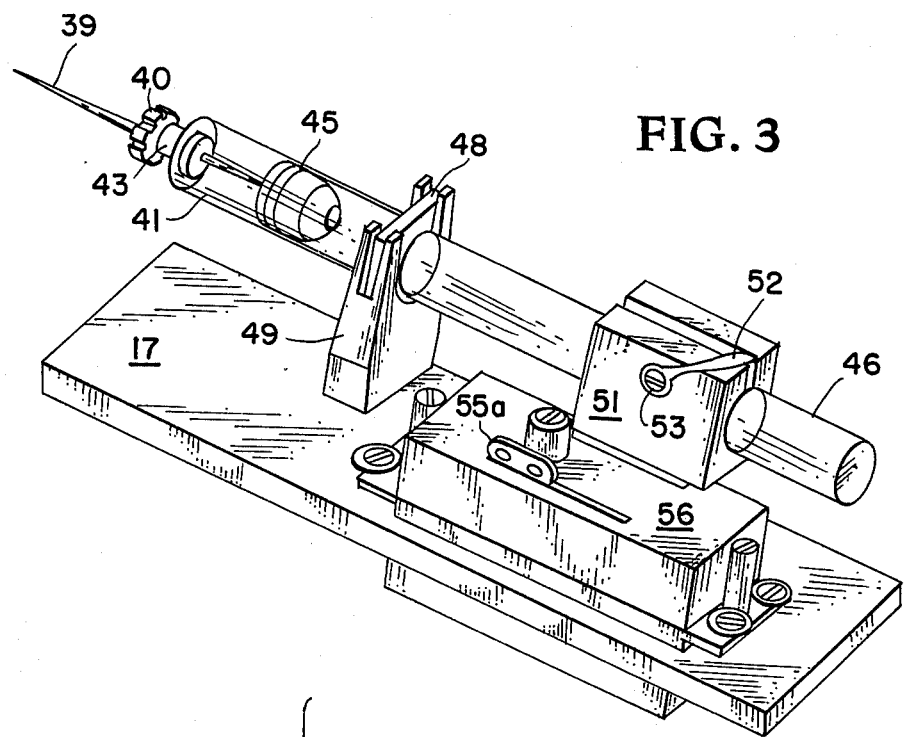
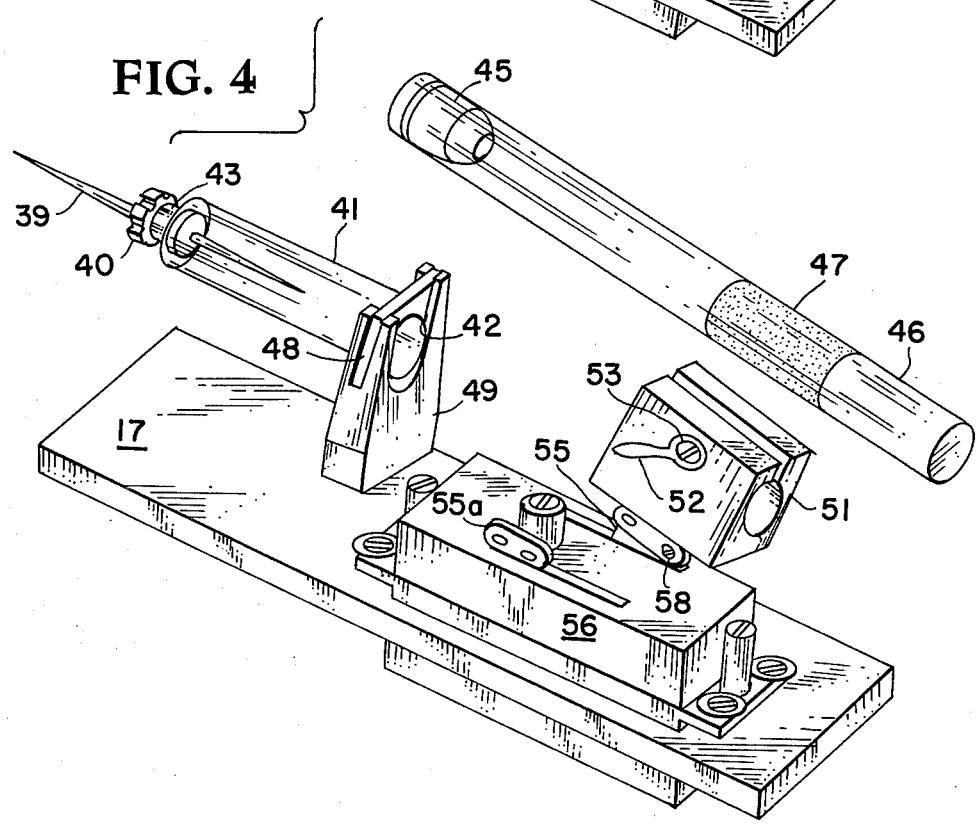

AUTOMATED SYRINGE SAMPLER

ORIGIN OF THE INVENTION

The invention described herein was made by an employee of the U. S. Government and may be manufactured and used by or for the Government for governmental purposes without the payment of any royalties thereon or therefor.

BACKGROUND OF THE INVENTION

This invention relates generally to a device for remote sampling of a fluid medium and relates particularly to a device for remote sampling of air or water in field pollution studies and the like.

Previously, sampling of fluid mediums in pollution studies and the like have involved the use of evacuated stainless-steel grab cylinders, manual collection using plastic sampling bags and a large syringe, and chemically trapping the pollutant in glass-bubbler solutions. Each of these sampling techniques have numerous disadvantages. For example, the grab cylinders are expensive to maintain, are bulky, and although they can be adapted to remote operation they require automated valves, tubing and subcontrol systems. Also, the cylinder walls will occasionally absorb a portion of the gas sample when low concentrations are involved.

Plastic sampling bags are not as costly as stainless-steel cylinders but are more difficult to adapt to remote operations and often leak or become accidently punctured. Collection of contaminates or pollutants using gas bubblers is of limited utility since they are easily broken or otherwise contaminated and are difficult to store and transport. Also, the liquid solutions have a limited shelf-life which could lead to erroneous test results.

There is therefore a definite need in the art for a simple, inexpensive, reliable, remote sampling device for use in obtaining test samples of a fluid medium from remote sites.

It is therefore an object of the present invention to provide an improved system for obtaining fluid samples from a remote location.

It is another object of the present invention to provide a simple remote sampling system that can be accurately operated by semi-skilled technicians.

It is a further object of the present invention to provide a system for sequentially obtaining multiple samples of a fluid medium at a remote site.

Another object of the present invention is to provide a system for collecting a plurality of fluid samples at a single location adaptable to be transported to a remote analysis site without danger of sample contamination.

According to one aspect of the present invention the foregoing and additional objects are attained by providing a housing disposed in a fluid medium and containing a removable rack therein with a plurality of identical sampling containers removably affixed to the rack and adapted to selectively entrap a sample of the ambient fluid medium in response to a remote signal. The sample containers housing the entrapped samples may be removed and transported to another site for analysis and clean sample containers placed in the system for subsequent sampling.

BRIEF DESCRIPTION OF THE DRAWINGS

A more complete appreciation of the present invention and many of the attendant advantages thereof will be readily apparent as the same becomes better understood with reference to the following detailed description when considered in connection with the accompanying drawings wherein:

FIG. 3 is an enlarged view of a single sample receiving container and the holding and actuation mechanism therefore;

FIG. 4 is a part-exploded view of the individual sample receiving mechanism shown in FIG. 3 illustrating the loading position of the parts.

DETAILED DESCRIPTION OF A PREFERRED EMBODIMENT

Figure 1:
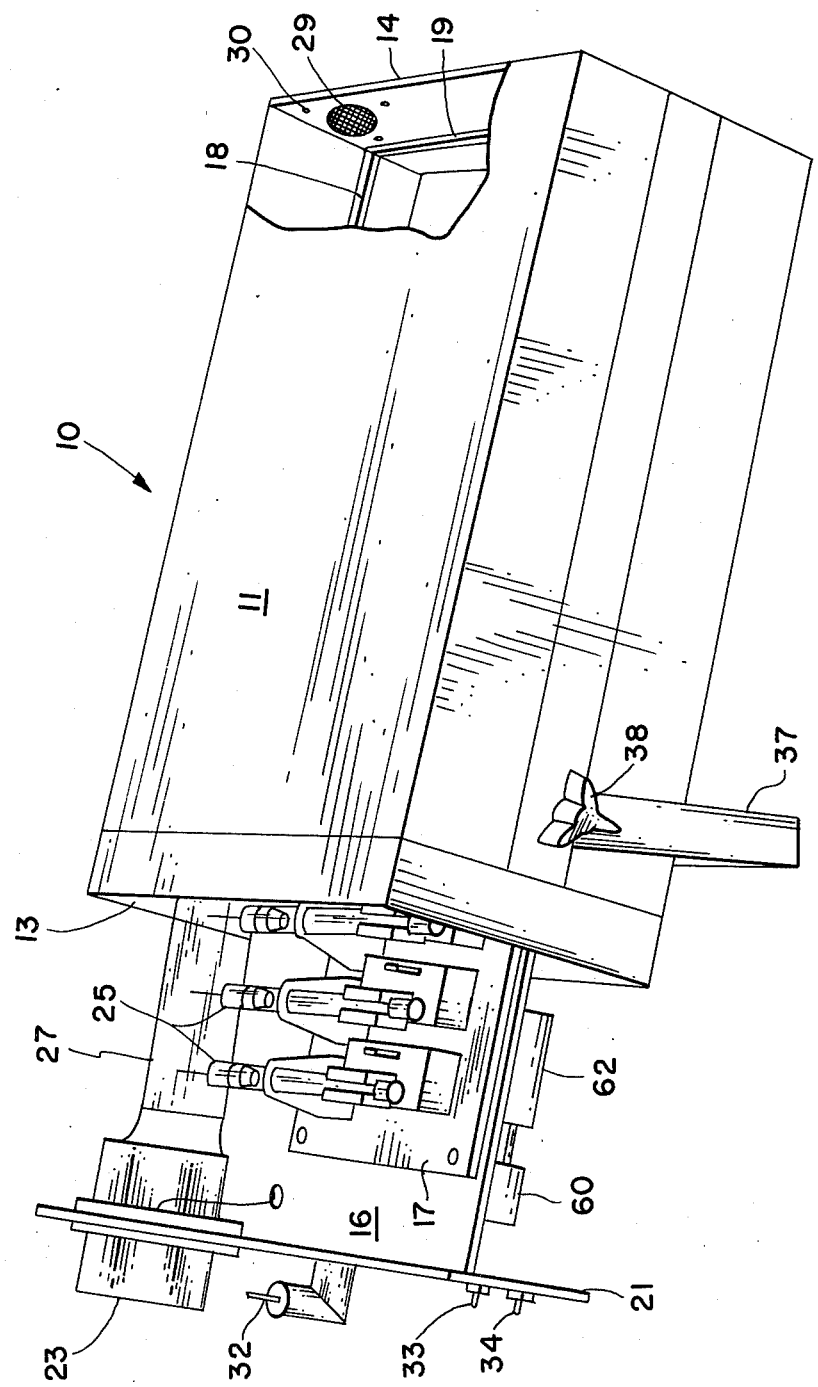
FIG. 1 is a perspective view of the sampler system according to the present invention with the sample container rack partially removed from the housing.

Referring now to the drawings and more particularly to FIG. 1 the sampling system of the present invention is generally designated by reference numeral 10. Sampling system 10 includes a housing 11 having an open end 13 and a closed end 14. A rack member 16 is slidably received along a pair of tracks or grooves 18 formed along the interior sidewall of housing 11. Only one groove is shown in FIG. 1, but the other is identical and formed along the opposite interior sidewall. One end of rack 16 is adapted to be received by retaining groove 19 formed along the interior surface of closed end 14 when rack 16 is completely positioned within housing 11. Retaining groove 19 is effectively a continuation of tracks 18. The opposite end of rack 16 is integrally attached to a cover or closure 21 which is attached to (by suitable bolts, not shown) and serves to seal the open end 13 of housing 11 when rack 16 is fully received therein.

The upper surface of rack 16 supports a base plate 17 having a plurality of individual sampling units 25 thereon, as will be further explained hereinafter. A suitable pump 23 is positioned extending through cover 21 and serves to assist in movement of the test fluid medium through housing 11 for sampling thereof. Pump 23 has an attached conduit 27 extending the length of housing 11 when cover 21 is secured thereto. Conduit 27 is adapted to abut against and circumscribe an entrance filter unit 29 disposed in the closed end 14 of housing 11. Filter unit 29 is secured to an opening in closed end 14 via suitable bolts 30.

An antenna 32 and a pair of switches 33 and 34 are disposed on the exterior surface of cover 21 and lead to the electrical circuitry 60 and 62 secured to the base of rack 16. Circuitry elements 60, 62 and others, not shown, serve to actuate sampling units 25 and pump 23 as will be further explained hereinafter.

A handle 37 is pivotally attached to housing 11 by a pair of knobs, one of which is shown and designated by reference numeral 38. Knobs 38 are threaddedly connected to housing 11 and, when tightened, will retain handle 37 in position. When relaxed or loosened, knobs 38 permit handle 37 to be pivoted to the desired position to facilitate transporting by hand and to angularly position housing 11, as shown in FIG. 1, or as so desired.

Figure 2:
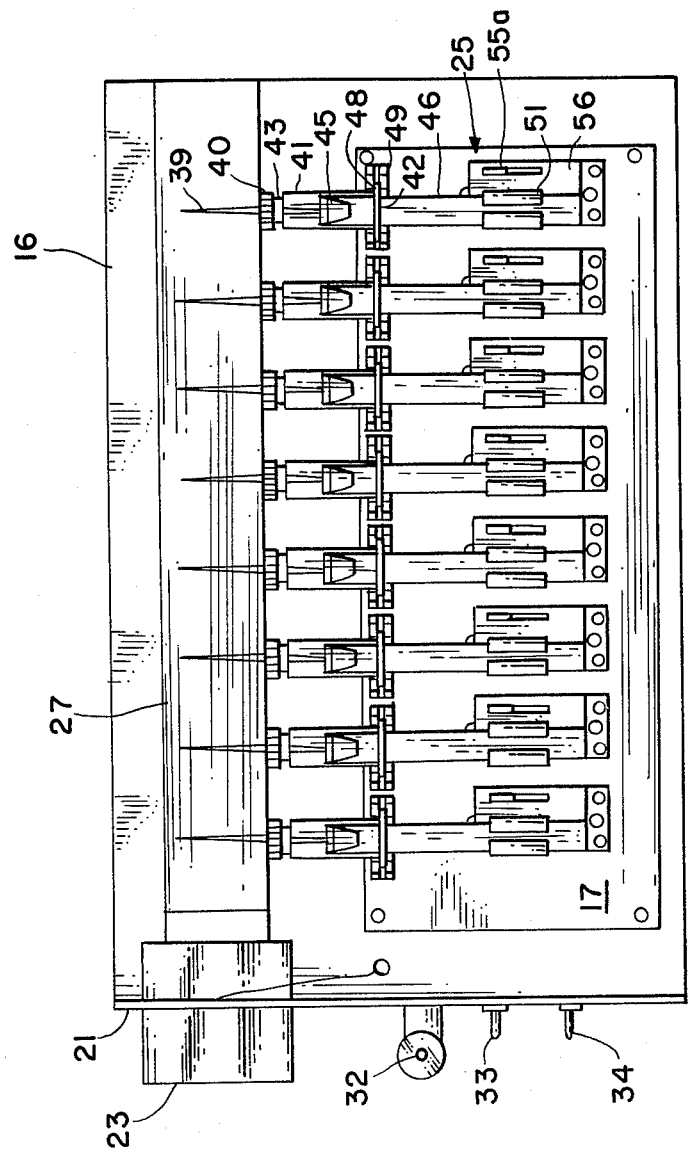
FIG. 2 is a view of the entire sample container rack removed from the system housing shown in FIG. 1.

Referring now more particularly to FIG. 2, it is seen that the preferred embodiment of the present invention employs a system of eight sampling units 25. Each sampling unit 25 includes a double-ended hollow needle 39, one end of which is received through the sidewall of conduit 27. Only one unit 25 and the parts thereof are designated in FIG. 2 for clarity and it is to be understood that each of the other seven units are of identical construction. The other end of needle 39 is disposed within a protective sleeve 41 and terminates adjacent a resilient septum or seal 45 mounted in the end of an evacuated tube 46. As shown in FIGS. 2–4, protective sleeve 41 has an open end 42 and a reduced diameter threaded end 43. Double-ended needle 39 is provided with an intermediate threaded connector 40 received by threaded end 43 of needle 39.

Protective sleeve 41 is provided with an enlarged diametrically disposed projection in the form of a pair of ears 48 adapted to be received by a bifuricated bracket 49 fixed to and extending vertically from base plate 17. Evacuated tube 46 is retained by an adjustable friction fit within the jaws of a bracket 51. A lever 52 extends from bracket 51 and is secured to a screw 53 that extends across the bracket jaws. When turned in a first direction lever 52 rotates screw 53 to loosen the bracket jaws and permit slidable removal or installation of tube 46. When lever 52 is rotated in the opposite direction screw 53 tightens or draws the jaws toward each other to firmly engage tube 46 for retention thereof.

Jawed bracket 51 is pivotally connected via connector pin or screw 58 to one of the linear movable actuator arms 55 of a sevo-mechanism 56. This pivotal connection permits jawed bracket 51 to be rotated about the pivot point connection 58 to assist in installing and removing evacuated tubes 46. As shown in FIG. 4 each evacuated tube 46 is provided with suitable indicia 47 thereon which defines the area of tube 46 that must be enclosed by jawed bracket 51 for the sampling unit to be operable. In the preferred embodiment this indicia is in the form of a shrink type plastic sleeve 47 which serves the function of providing some cushioning effect for the evacuated glass tube portion confined within the jaws of bracket 51, aids in the frictional connection thereof and serves as a guide to the semi-skilled operator for exact positioning of tube 46. Servo-mechanism 56 is a commercially available unit Model KPS-11, Series 76 Kraft Systems, Inc. and is provided with a pair of oppositely moving actuator arms 55 and 55a and only one of which is utilized in the present inention. As shown in FIGS. 3 and 4 servo units 56 extend through and are each secured to base plate 17 via a plurality of suitable screws or bolts (not designated). Base plate 17 is secured to rack 16 by suitable bolts or screws (also not designated) over an opening 22 therein so as to expose the depending portion of each servo 56 to the electrical circuitry (FIG. 5).

The double-ended needle 39 and its component parts are available from Becton, Dickinson and Company as "Vacutainer" brand, Catalog No. B-D-4892 and the glass evacuated sample tube is also available from this company as catalog item number B-D-4880.

The pump 23 in the illustrated embodiment is a four-bladed fan motor available from the Rotron Manufacturing Company, Woodstock, WV, Aximax-2, series 464YH, Part No. 026952, RPM 10200.

Figure 5:
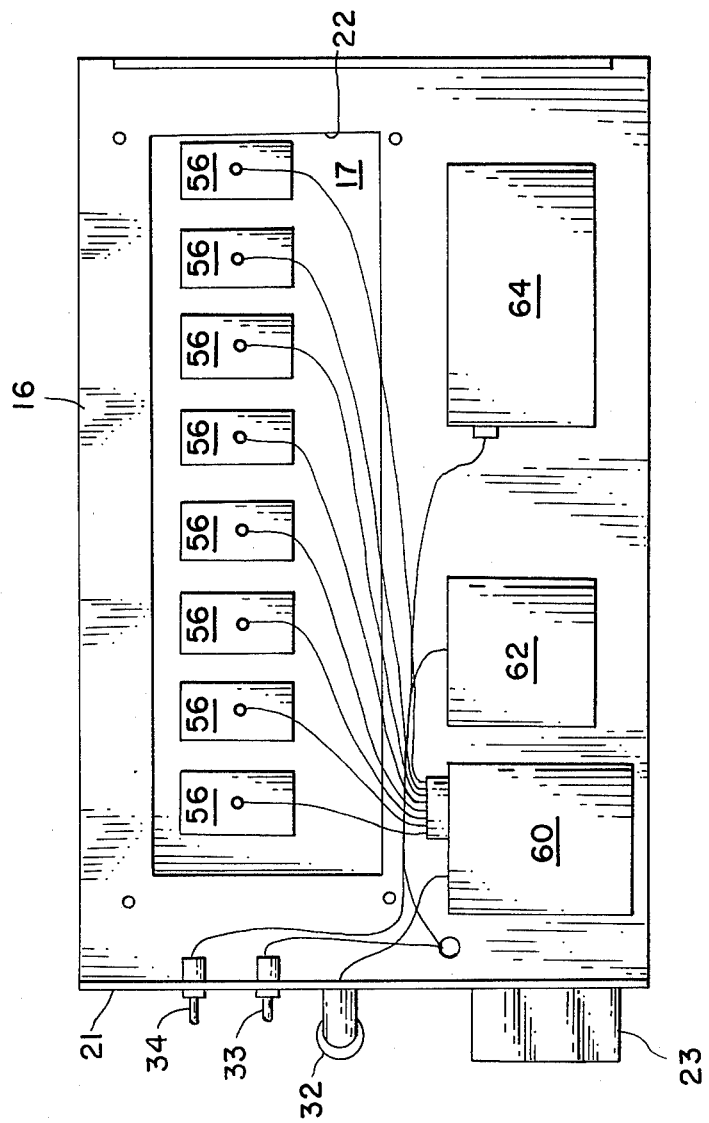
FIG. 5 is a bottom view of the sample container rack and associated electrical components for the present invention.

Referring now more particularly to FIG. 5 the electrical components for operating the sampling system includes a radio receiver component 60 and associated battery back 62 for actuating sampling units 25. A second battery pack 64 serves to provide power for pump 23. The radio receiver component 60 is a standard Kraft "series seventy-five" receiver and the battery pack 62 therefor utilizes four 1.35v "nicad" rechargeable batteries. Receiver 60 operates on eight single frequency channels (eight pulse widths) or one for each of servo unit 56. The remote transmitter providing the radio signal to receiver 60 via antenna 32 is a single frequency transmitter and, as is conventional in the art, may employ a separate switch for each pulse width or any number of channels to be actuated by a single switch. Also, a single switch at the transmitter may be used to actuate a timer to send individual signals to receiver 60 for each of the servo-mechanisms 56.

OPERATION

The operation of the present invention is now believed apparent. Sampling system 10 is assembled as shown in FIGS. 1 and 2 and transported to the test site encased within housing 11 and positioned at the desired angle relative to the horizontal by adjusting handle 37. Switch 33 is actuated to supply power to pump 23 from battery pack 64 and switch 63 is actuated to provide power to servo-mechanisms 56 via receiver 60. Servo-mechanisms 56 are not actuated until a signal is transmitted from a remote transmitter, (not shown) picked up by antenna 32 to receiver 60 and relayed individually to each of the servo-mechanisms 56. When servo-mechanism 56 is energized, actuator arm 55 and its attached jawed bracket 51 move evacuated tube 46 toward needle 39. Septum 45 of tube 46 is punctured by the open end of needle 39 contained within protective sleeve 41 and the fluid medium to be tested enters the end of needle 39 disposed within conduit 27. The vacuum in evacuated tube 46 causes the test fluid to be drawn through needle 39 until the pressure within tube 46 equals that in conduit 27 or until the signal to servo 56 is received. When the sample is obtained the signal to servo 56 is reversed and actuator arm 52 moves jawed bracket 51 and tube 46 back to the original position permitting septum 45 to expand and close the hole formed therein by needle 39 as tube 46 is withdrawn from the needle.

Tube 46 containing the test sample may then be removed by a semi-skilled technician and replaced by another evacuated tube for subsequent sampling in the field with the collected samples being transported to the analysis site. For ease in installing evacuated tubes 46 (and removing collected sample tubes), lever 52 and its attached screw 53 are rotated in a first direction to separate the jaws on bracket 51 sufficient to permit an easy sliding fit of tube 46 within the jaws. In the preferred embodiment the rotation of lever 52 and screw 53 is approximately one-half a turn. In some applications lever 52 may be eliminated and screw 53 adjusted directly. Tube 46 is then inserted within bracket 51 with the indicia or plastic tubing 47 thereon positioned aft of bracket 51 so as to permit pivoting of bracket 51 to the operative position shown in FIG. 3. Tube 46 is then moved into protective sleeve 41 until indicia 46 is completely within bracket 51 to thereby position septum 46 adjacent the end of needle 39 within protective sleeve 41. Lever 52 is then rotated in the opposite direction to cause screw 53 to tighten the jaws on bracket 51 and thereby firmly retain tube 46 from further relative movement therein.

When it is desired to use pump 23 only during sampling, one of the eight channels in receiver 60, e.g., channel 1 could be used to actuate pump 23 in lieu of the separate switch 34. Also, the specific pump 23 in the illustrated embodiment would be practical only for air or gas sampling and a different type conventional pump would be used, if needed, in water pollution studies although normally the water flow would be adequate to obviate the need for any pump.

Although the invention has been described relative to a specific embodiment thereof, it is not so limited and many modifications and variations thereof will be readily apparent to those skilled in the art in the light of the above teachings. For example, although the specific illustrated embodiment shows needle 39 and its protective cover remaining stationary while evacuated tube 46 moves, obviously, the system could also be arranged for tube 46 to remain fixed and needle unit 39 designed to move reciprocally therewith if so desired. In addition, only actuator arm 55 of servo 56 is used for work in the illustrated embodiment and in some instances it may be desirable to attach a secondary sampling system to actuator arm 55a for simultaneous operation. Also, the radio receiver-transmitter could be eliminated and each of servos 56 actuated separately or collectively by direct switch control, when so desired. These and other variations and modifications of the illustrated embodiment will become readily apparent to those skilled in the art in the light of the above teachings without departing from the spirit and scope of the present invention. It is therefore to be understood that within the scope of the appended claims the invention may be practiced otherwise than as specifically described.

What is claimed as new and desired to be secured by Letters Patent of the Unites States is:

1. Apparatus for remotely sampling a fluid medium comprising:
    at least one evacuated sample receiving container disposed within the fluid medium to be sampled;
    a resilient septum sealingly disposed within an opening in said sample receiving container;
    a double ended hollow needle disposed such that one end thereof is adjacent to said resilient septum;
    signal responsive means for effecting selective relative linear movement of said sample container and said double ended needle toward and away from each other whereby when said sample container and said double ended needle move relatively toward each other said double ended needle will penetrate said resilient septum and permit the fluid medium to enter said evacuated sample container and when said sample container and said double ended needle are linearly moved relatively away from each other said needle will be removed from said resilient septum to seal the fluid sample within said container;
    said signal responsive means being an electrically actuated servo-mechanism;
    a base plate for said apparatus;
    means for fixedly securing said servo-mechanism to said base plate;
    an exposed linearly movable actuator arm disposed on said servo-mechanism;
    a sample container bracket secured to said actuator arm; and,
    said bracket being provided with a pair of jaws serving to receive said sample container.

2. The apparatus as in claim 1 wherein said bracket is pivotally attached to said actuator arm to facilitate positioning of said sample container between said jaws.

3. The apparatus as in claim 1 including indicia on said sample container indicating the optimum relative position thereof with said jaws when said container is positioned within said jaws.

4. The apparatus as in claim 1 including adjustable means for frictionally retaining said sample container within said jaws.

5. The apparatus as in claim 1 wherein a threaded connector is fixedly attached intermediate to the ends of said double-ended needle, and a tubular protective sleeve is provided around the end of said double ended needle disposed adjacent to said resilient septum, said tubular protective sleeve having a first end sealingly receiving said threaded connector and a second open end extending a distance beyond the end of said double ended needle disposed adjacent to said resilient septum, said second open end of said tubular protective sleeve being provided with an enlarged diametric extension thereon, a sleeve retaining bracket fixedly attached to and vertically extending from said base plate; and,
    means on said bracket for slidably receiving said enlarged diametric extension for releasably retaining said double-ended needle adjacent said resilient septum.

6. An automated syringe fluid sampler system comprising in combination:
    a housing disposed in a fluid test medium and containing sampler system components, said housing having a closed end and an open end,
    a slidable rack member slidable received by said housing through the open end thereof,
    guide track means within said housing for maintaining the position of said rack member therein,
    a closure for the open end of said housing integrally secured to said slidable rack so as to close said open end of said housing when said rack is positioned therein;
    a plurality of signal responsive sampling units secured to said rack member, and
    means for energizing said signal responsive means to cause each said signal responsive sample unit to extract a fluid sample from the fluid test medium.

7. The sampler system of claim 6 wherein said plurality of signal responsive sampling units comprise a series of servo-mechanisms, each said servo-mechanism having a linear movable actuator arm, an evacuated sample tube having a resilient septum therein movable by said actuator arm, a double-ended hollow needle supported by said rack and having a first end thereof in fluid communication with the fluid test medium and a second end thereof in position to penetrate said resilient septum when said sample tube is moved by said actuator arm, whereby upon penetration of said septum a sample of the test fluid will flow through said double-ended needle into said evacuated sample tube and upon movement of said actuator arm in the opposite direction said double-ended needle will be removed from said septum and seal the fluid sample obtained within said sample tube for subsequent testing.

8. The sampler system of claim 6 including means for inducing continuous fluid flow of the test medium through said housing and adjacent each of said sampling units during fluid sampling of the test medium.

9. The sampler system of claim 8 wherein said means for inducing continuous fluid flow of the test medium includes a conduit disposed within and extending the length of said housing, a pump extending through said heating closure and in fluid communication with one end of said conduit, an entrance filter disposed in an opening formed in said closed end of said housing and circumscribed by the other end of said conduit, and each of said sampling units extending through a sidewall of said conduit so as to be in fluid communication with the interior of said conduit.

* * * * *